United States Patent
Kim et al.

(10) Patent No.: US 11,872,310 B2
(45) Date of Patent: Jan. 16, 2024

(54) PREPARATION FOR ORAL CAVITY

(71) Applicant: LG Household & Health Care Ltd., Seoul (KR)

(72) Inventors: Ji-Young Kim, Daejeon (KR); Jae-Hyun Ahn, Daejeon (KR); In-Ho Lee, Daejeon (KR)

(73) Assignee: LG Household & Health Care Ltd.

( * ) Notice: Subject to any disclaimer, the term of this patent is extended or adjusted under 35 U.S.C. 154(b) by 0 days.

(21) Appl. No.: 17/148,043

(22) Filed: Jan. 13, 2021

(65) Prior Publication Data

US 2021/0128464 A1 May 6, 2021

Related U.S. Application Data

(62) Division of application No. 16/069,325, filed as application No. PCT/KR2017/000409 on Jan. 12, 2017, now Pat. No. 10,925,830.

(30) Foreign Application Priority Data

| Jan. 13, 2016 | (KR) | 10-2016-0004353 |
| Feb. 2, 2016 | (KR) | 10-2016-0012964 |
| Mar. 11, 2016 | (KR) | 10-2016-0029820 |

(51) Int. Cl.
*A61K 8/02* (2006.01)
*A61K 8/21* (2006.01)
(Continued)

(52) U.S. Cl.
CPC .............. *A61K 9/06* (2013.01); *A61K 8/25* (2013.01); *A61K 8/733* (2013.01); *A61K 8/8129* (2013.01); *A61K 9/0056* (2013.01); *A61K 9/0063* (2013.01); *A61K 31/055* (2013.01); *A61K 31/155* (2013.01); *A61K 31/194* (2013.01); *A61K 31/355* (2013.01); *A61K 33/16* (2013.01); *A61K 33/30* (2013.01); *A61K 33/40* (2013.01);
(Continued)

(58) Field of Classification Search
None
See application file for complete search history.

(56) References Cited

U.S. PATENT DOCUMENTS

| 5,989,569 A | 11/1999 | Dirksing et al. |
| 2003/0012747 A1 | 1/2003 | Peterson |

(Continued)

FOREIGN PATENT DOCUMENTS

| CA | 2403489 C | 5/2011 |
| EP | 0914832 A1 | 5/1999 |

(Continued)

OTHER PUBLICATIONS

Search report from International Application No. PCT/KR2017/000409, dated Jun. 30, 2017.

(Continued)

*Primary Examiner* — Brian Gulledge
(74) *Attorney, Agent, or Firm* — Lerner David LLP

(57) ABSTRACT

The present invention provides a preparation for attaching to teeth or tooth peripheries. The preparation for attaching to teeth or tooth peripheries of the present invention can give high adhesive force to the desired site despite interproximal space or curves of teeth. It is easy to hand while controlling drug release.

7 Claims, 4 Drawing Sheets

PVM/MA(Gantrez S-97)

Alginate-Calcium Complex

(51) Int. Cl.

| | | |
|---|---|---|
| *A61K 8/67* | (2006.01) | |
| *A61K 8/97* | (2017.01) | |
| *A61K 9/00* | (2006.01) | |
| *A61K 9/06* | (2006.01) | |
| *A61K 9/08* | (2006.01) | |
| *A61K 33/16* | (2006.01) | |
| *A61K 47/14* | (2017.01) | |
| *A61K 47/38* | (2006.01) | |
| *A61K 36/575* | (2006.01) | |
| *A61Q 11/00* | (2006.01) | |
| *A61K 8/81* | (2006.01) | |
| *A61K 31/194* | (2006.01) | |
| *A61K 36/23* | (2006.01) | |
| *A61K 33/40* | (2006.01) | |
| *A61K 33/30* | (2006.01) | |
| *A61K 31/355* | (2006.01) | |
| *A61K 8/73* | (2006.01) | |
| *A61K 8/25* | (2006.01) | |
| *A61K 31/055* | (2006.01) | |
| *A61K 31/155* | (2006.01) | |
| *A61K 33/42* | (2006.01) | |
| *A61K 47/10* | (2017.01) | |
| *A61K 47/12* | (2006.01) | |
| *A61K 47/02* | (2006.01) | |
| *A61K 47/32* | (2006.01) | |
| *A61K 47/36* | (2006.01) | |

(52) U.S. Cl.
CPC .............. *A61K 33/42* (2013.01); *A61K 36/23* (2013.01); *A61K 36/575* (2013.01); *A61K 47/10* (2013.01); *A61K 47/12* (2013.01); *A61Q 11/00* (2013.01); *A61K 47/02* (2013.01); *A61K 47/32* (2013.01); *A61K 47/36* (2013.01)

(56) References Cited

U.S. PATENT DOCUMENTS

| | | | |
|---|---|---|---|
| 2005/0232982 A1 | 10/2005 | Ihara et al. | |
| 2008/0305168 A1 | 12/2008 | Moon et al. | |
| 2014/0373853 A1* | 12/2014 | Circo | ................... A63B 71/085 128/862 |
| 2021/0128464 A1 | 5/2021 | Kim et al. | |

FOREIGN PATENT DOCUMENTS

| | | | | |
|---|---|---|---|---|
| JP | 2019501941 A | | 1/2019 | |
| KR | 20040009547 A | | 1/2004 | |
| KR | 20060021967 A | | 3/2006 | |
| KR | 20060059403 A | | 6/2006 | |
| KR | 20060094713 A | | 8/2006 | |
| KR | 100623859 B1 | | 9/2006 | |
| KR | 10-0662203 | * | 12/2006 | ............... A61K 8/19 |
| KR | 100662203 B1 | | 12/2006 | |
| KR | 100814250 B1 | | 3/2008 | |
| KR | 101148470 B1 | | 5/2012 | |
| KR | 20150111667 A | | 10/2015 | |
| WO | 03037276 A1 | | 5/2003 | |
| WO | 03070218 A1 | | 8/2003 | |
| WO | 2007066837 A1 | | 6/2007 | |
| WO | 2010117266 A1 | | 10/2010 | |

OTHER PUBLICATIONS

Supplementary Partial European Search Report for Application No. EP 17738649.7 dated Jul. 29, 2019, 6 pages.

Chinese Search Report for Application No. 201780006327.1 dated Mar. 31, 2021, pp. 1-2.

Zhang, G. , "Pharmaceutical Excipient Application Technology", Chinese Medicine Department, Dec. 1991, p. 382, ISBN 7.

* cited by examiner

PVM/MA(Gantrez S-97)      Alginate-Calcium Complex

PREPARATION FOR ORAL CAVITY

CROSS-REFERENCE TO RELATED APPLICATIONS

This application is a divisional of U.S. application Ser. No. 16/069,325, filed on Jul. 11, 2018, which is a national phase entry under 35 U.S.C. § 371 of International Application No. PCT/KR2017/000409, filed on Jan. 12, 2017, which claims priority to from Korean Patent Application No. 10-2016-0012964 filed on Feb. 2, 2016, Korean Patent Application No. 10-2016-0004353 filed on Jan. 13, 2016, and Korean Patent Application No. 10-2016-0029820 filed on Mar. 11, 2016 in the Republic of Korea, the disclosures of which are incorporated herein by reference.

TECHNICAL FIELD

The present invention relates to a mouth band which can be attached to teeth or tooth peripheries to deliver a medicinal ingredient into the oral cavity. More specifically, the present invention relates to a mouth band capable of effectively delivering the medicinal ingredient into the oral cavity by having excellent adhesive force and securing sufficient attachment time.

BACKGROUND OF THE INVENTION

In order to deliver an oral medicinal ingredient into the oral cavity, the contact time with a medicinal ingredient and the delivery amount play an important role.

Paste formulations such as toothpaste have a disadvantage that it is difficult to provide sufficient contact time at the target site due to insufficient viscosity and high solubility, and mouth trays intended for intraoral drug delivery have a disadvantage that they have a strong sense of foreign body and difficult to deliver a drug locally due to their shape characteristics. Patch type or strip type is thin, so it is difficult to deliver sufficient amount of a medicinal ingredient, and flexibility is low, so there is a disadvantage that it is difficult to be adhered to interproximal space, boundary area between gums and teeth, and the like.

In order to solve the adhesion problem to the interproximal space, boundary area between gums and teeth and the like, Korean Patent No. 10-0623859 developed a delivery system for a tooth whitening component using in situ gelling, but there was a disadvantage that it is necessary to use a separate backing layer because it is highly flowable when applied to the tooth surfaces. Further, WO 2003/037276 discloses a preparation to be sprayed in the oral cavity due to its low initial viscosity, but there was a problem that the difference between the normal storage temperature (especially in summer) and the temperature in the oral cavity is small and it is difficult to remove it because the phase transition does not occur rapidly unless it is applied very thin.

U.S. Pat. No. 5,989,569 discloses about applying a drug to the surface of a strip and delivering the drug by pressure, but there were problems that the medicinal ingredient is temporarily released because the drug is applied on the surface of the strip and adhered to teeth as it is, and it may cause strong stimulus in the gums around the teeth. Further, there was a disadvantage that physical properties, in particular, flexibility, of the drug to be applied are different from those of the strip, and therefore, adhesion to interproximal space is difficult.

The inventors of the present invention have studied for a long time to develop a novel form of a preparation, which can effectively deliver a drug into the oral cavity with convenience of use, thereby completing the present invention. In particular, the present inventors have been trying to consider a formulation suitable for use under a specific condition, i.e., in the oral cavity while improving adhesive force even to interproximal space or curves of teeth.

SUMMARY OF THE INVENTION

In order to solve the above problems, the present invention is directed to providing a novel form of a preparation for attaching to the oral cavity which is easy to be adhered to the desired site in the oral cavity and can secure sufficient contact time.

Further, the present invention is directed to providing a preparation in the form that can be freely changed before use, and can be adhered well to interproximal space or a boundary area between gums and teeth.

The present invention is directed to providing a novel form of a preparation, which can be excellently adhered not only to the buccal surface or boundary area between gums and teeth but also to interproximal space without flowing down at the beginning of attachment, and can be removed from teeth without any irritation at the time of removal after the drug is fully released.

The present invention is directed to providing a novel form of an oral preparation, which is soft and flexible, and can be used conveniently because it does not flow down, and also can secure sufficient contact time with the target site.

DETAILED DESCRIPTION OF THE INVENTION

The present invention provides a preparation for attaching to teeth or tooth peripheries.

In one embodiment of the present invention, the preparation for attaching to teeth or tooth peripheries can be provides in the form of mouth band.

The preparation for attaching to teeth or tooth peripheries according to one embodiment of the present invention is a shine hydrogel containing synthetic; silica, and therefore it can be adhered in the oral cavity.

The term 'mouth band' used herein may mean a formulation that can be adhered to the teeth, gums, buccal and the like in the oral cavity. For example, it can be attached in the form of a band. The mouth band may have, for example, a rectangular shape, a round shape and the like, and may be formed in various shapes in consideration of a target site, attachment time and the like. It may be provided in the form of clay-like dough without any specific shape as needed.

The inventors of the present invention have studied for a formulation of an oral preparation, which can easily transformed even by small pressure so as to deliver a drug up to interproximal space, and can have enough adhesive force and shape retention force not to flow down from the attachment site, thereby completing the present invention.

The term 'slime hydrogel' used herein is used to mean hydrogel with excellent elongation percentage and excellent stretchiness. Hydrogel forms a three-dimensional polymeric network and is swellable. The hydrogel has the ability to absorb fluid and can release a drug at a constant concentration, but it is stiff so that it is difficult to be adhered to curves or gaps of teeth and can be broken well when the hydrogel is stretched.

The slime hydrogel is excellent in malleability like jelly, stretches well, and has a three-dimensional polymeric network. Therefore, it is a novel formulation with excellent drug release control and free-shape transformation.

In one embodiment of the present invention, the slime hydrogel may mean a condition that is more resilient than a three-dimensional network formed by hydrogen bonding of —OH groups of PVA and salts (for example, borate), and is shape-transformable. The slime hydrogel is a formulation that is less flowable than slime and has more shape retention force, but is more flexible and stretchable than hydrogel. It may have moderate shape transformability between slime and hydrogel.

In one embodiment of the present invention, the slime hydrogel formulation may be achieved by synthetic silica or an alginate compound.

Silica is an inorganic thickener having very small and uniform size, and it is water-insoluble and excellent dispersion force in aqueous solution. Although it was confirmed that the silica can be excellent in achieving slime hydrogel formulation because it has hydrogen bonding property thereby increasing thixotropic, the present invention is not to be construed as limited to such theory.

The synthetic silica may be at least one selected from silica powder, fumed silica, precipitated silica, colloidal silica, aerogel and silica sol, and preferably it may be fumed silica. The fumed silica may be, for example, AEROSIL® types from EVONIK such as AEROSIL® 200, AEROSIL®300 and the like. The synthetic silica may be contained in an amount of 0.1 wt % to 20 wt % based on the dry weight of the preparation for attaching to teeth or tooth peripheries, and it may be contained in an amount of 0.5 wt % to 10 wt %.

Within the above content range, it may be preferred in terms of rheology of the formulation.

In one embodiment of the present invention, the slime hydrogel may form hydrogen bonds by reacting polyvinyl alcohol (PVA) and —OH groups of the polyvinyl alcohol. The polyvinyl alcohol is a polymer whose in vivo stability is proven and is a film-forming polymer capable of forming a thin film. The —OH group contained in the polyvinyl alcohol has an excellent elastic property at the time of gel formation by a bridge structure formed by hydrogen bonds with salts, and the desired formulation property of the present invention can be achieved by the use of the synthetic silica of the present invention.

The salt forming hydrogen bonds with —OH groups of the polyvinyl alcohol may be borate, phosphate or a mixture thereof, and the borate may include potassium borate, sodium borate and the like, and the phosphate may include tetrasodium pyrophosphate, tetrapotassium pyrophosphate and the like.

Preferably, when considering compatibility between the PVA and the synthetic silica, the salt may be sodium borate.

The preparation according to another embodiment of the present invention may be attached to the oral cavity as a slime hydrogel containing an alginate compound.

It was confirmed that the hydrogen bonding property of the alginate compound affects the formation of the slime hydrogel, and therefore, it can exert an excellent effect in achieving the formulation giving the thixotropy property of the slime hydrogel. However, the present invention is not to be construed as limited to such theory. Preferably, the alginate compound may be contained in an amount of 0.1 wt % to 20 wt % based on the dry weight of the preparation, and the amount of preferably 5 wt % or less, more preferably 2 wt % or less, and most preferably 0.5 wt % or less is preferred because the slime hydrogel can be formed uniformly within the range.

The alginate compound may include calcium alginate, potassium alginate, sodium alginate, triethanolamine alginate or a mixture thereof.

The preparation of the present invention may comprise a medicinal ingredient which can be delivered into the oral cavity. The medicinal ingredient may include all of the medicinal ingredients that can be delivered into the oral cavity, and may preferably include a medicinal ingredient intended to treat oral diseases or to prevent or improve oral diseases and the like.

The medicinal ingredient may include, for example, an ingredient for tooth whitening, an ingredient for preventing cavity containing a fluoride ion source, an ingredient for inhibiting tartar formation, an anti-inflammatory ingredient, an anti-bacterial ingredient, other vitamins, mineral ingredients and the like. Further, it may also include ingredients for improving sensitive teeth and for relieving its symptoms, and the like. More specifically, for example, it may include: at least one fluoride ion source selected from the group consisting of sodium fluoride, stannous fluoride, indium fluoride, amine fluoride and sodium monofluorophosphate; a remineralization agent containing hydroxyapatite; and an ingredient for tooth whitening selected from hydrogen peroxide, carbamide peroxide, calcium peroxide, perborate, percarbonate, peroxyacid, persulfate, calcium chlorite, barium chlorite, magnesium chlorite, lithium chlorite, sodium chlorite or a mixture thereof. For enhancing whitening effect, a condensed phosphate can be used together with peroxides. The condensed phosphate, which can be used, may be at least one of tetrasodium pyrophosphate (TSPP), sodium acid pyrophosphate (SAPP), sodium tripolyphosphate (STP), sodium potassium pyrophosphate, tetrapotassium pyrophosphate, acidic sodium metaphosphate and acidic sodium polyphosphate, and it may be used together with peroxides. Such condensed phosphate also can be used for removing tartar or inhibiting tartar formation. Further, it can also contribute to the improvement of whitening effect by removing the metal which affects the stain formation of teeth as a chelating agent. The medicinal ingredient may include an anti-bacterial agent including triclosan, chlorhexidine, alexidine, hexetidine, sanguinarine, benzalkonium chloride, salicylanilide, domiphen bromide, cetylpyridinium chloride (CPC), tetradecylpyridinium chloride (TPC) or a mixture thereof; an anti-inflammatory agent including aspirin, ketorolac, flurbiprofen, piroxicam, meclofenamic acid or a mixture thereof; thiamine, riboflavin, nicotinic acid, pantothenic acid, pyridoxine, biotin, folic acid, vitamin B12, lipoic acid, ascorbic acid, vitamin A, vitamin D, vitamin E, vitamin K or a mixture thereof; or a mixture thereof, but not limited thereto. Further, the drug effective for preventing and improving periodontal diseases may be titrated extract of *Zea Mays* L. unsaponifiable fraction, Magnoliae Cortex extract, Myrrha, Rhatany, Chamomile, policresulen, titrated extract of Centella Asiatica, nutmeg extract, dexpanthenol, β-sitosterol, acetyl salicylic acid and the like alone, or a mixture thereof of a certain mixing ratio. The ingredient for improving and relieving sensitive teeth symptoms may be zinc chloride, potassium phosphate, potassium diphosphate, calcium chloride, oxalic acid, potassium oxalate, ferric oxalate, vitamin E and the like alone, or a combination of two or more thereof.

The medicinal ingredient may be present as homogeneously or inhomogeneously dispersed in the slime hydrogel of the preparation.

The preparation according to one embodiment of the present invention may further comprise a material, which can help release of the medicinal ingredient dispersed in the slime hydrogel, and for example, the material for helping drug release may be any material that can form a channel, a porous structure or bubble (foam) in the formulation. For example, it may comprise any one selected from the group consisting of i) acid such as acetic acid, lactic acid, malic acid, gluconic acid, ascorbic acid and the like or a water-soluble salt thereof, e.g., sodium citrate and ii) base such as sodium hydroxide (NaOH), potassium hydroxide (KOH), sodium bicarbonate (baking soda) and sodium carbonate. Preferably, the acid may be acetic acid, and the base may be sodium carbonate, and more preferably, those may be sodium citrate and sodium bicarbonate, which are an acid and a base mainly used in toothpaste.

The preparation according to one embodiment of the present invention may be present as slime hydrogel itself, or may be present in the form in which a supporter (for example, a water-insoluble film) and the like are further attached. When it is attached to teeth or tooth peripheries, it may further comprise a backing layer (backing film) as needed.

The backing layer may contact to an unwanted site while attaching the preparation according to one embodiment of the present invention. Thus, the backing layer may serve to prevent the problem. The backing layer may include a water-insoluble polymer, generally used in an oral film, and for example, polyethylene (PE), polypropylene (PP), ethylene vinyl acetate (EVA), cellulose acetate phthalate, shellac, polyvinyl acetate, ethyl cellulose, polymethyl methacrylate, methacryloylethyl betain/methacrylate copolymer (Yukaformer; Manufacturer: Mitsubishi), methacrylic acid copolymer (Eudragit L 100, Eudragit L 12,5, Eudragit L 100-55, Eudragit L 30D-55), aminoalkyl methacrylate copolymer (Eudragit E 100, Eudragit E 12,5, Eudragit RL 100, Eudragit RL 30D) and the like may be used.

The term 'tooth peripheries' used herein is generally a concept involving a region represented by gums, and may be used to mean including all of the mucosal regions around teeth. The tooth peripheries can be used to mean covering the region where a medicinal ingredient for intra-oral delivery can be delivered together with the teeth when the preparation is applied to the teeth in the structure of the preparation. Herein, 'teeth or tooth peripheries' is used together with 'teeth', and it may be understood herein to include both the teeth and the tooth peripheries even if it is described only as 'teeth'.

In one embodiment of the present invention, the preparation can be easily removed from teeth at the time of removal after drug release is completed, and it may be removed with very little residue left on the surface. In the case of containing the synthetic silica according to one embodiment of the present invention, adhesive force to teeth may be increased by mixing polyvinyl alcohol and sodium borate. Further, when removing the preparation after drug release is completed, it may be conveniently removed without leaving sticky on the tooth surfaces.

In another embodiment of the present invention, the present invention provides an oral preparation for attaching to teeth or tooth peripheries comprising a phase transition compound and a polymer which is mixed with the phase transition compound and can control hardening rate of the phase transition compound. The preparation may comprise a medicinal ingredient which can be delivered into the oral cavity. After the preparation is attached to teeth or tooth peripheries, the active ingredient contained in the preparation may be released and delivered to the desired site in the oral cavity.

In general, in the case of a phase transition formulation, when the first formulation and the second formulation meet and phase transition occurs, it is present as a fixed mass. The inventors of the present invention have confirmed that when using the ingredient controlling phase transition rate used in the present invention together, a novel form of a preparation, which is effective to drug release by controlling the hardening rate of the phase transition compound, can be provided, thereby completing the present invention.

The inventors of the present invention have studied for a long time to develop a novel form of a preparation, which can effectively deliver a drug into the oral cavity with convenience of use, thereby completing the present invention.

The conventional phase transition formulation generally forms a lump after completion of phase transition and then removed by peel-off method. When using the material of controlling phase transition rate according to one embodiment of the present invention together, the formulation may have a structure in which small lumps, rather than a single lump, are united by weak bonds at the time of removal, and therefore, it can be removed by brush-off method as if brushing with a tooth brush. Namely, the present invention is characterized in that the preparation of the present invention can be removed from the tooth surfaces through tooth brushing to give freshness in the oral cavity after use.

The term 'tooth peripheries' used herein is generally a concept involving a region represented by gums, and may be used to mean including all of the mucosal regions around teeth. The tooth peripheries can be used to mean covering the region where a medicinal ingredient for intra-oral delivery can be delivered together with the teeth when the preparation is applied to the teeth in the structure of the preparation. Herein, 'teeth or tooth peripheries' is used together with 'teeth', and it may be understood herein to include both the teeth and the tooth peripheries even if it is described only as 'teeth'.

The term 'preparation' used herein means to a product made by processing the medicinal ingredient to secure its therapeutic effect without affecting effectiveness of the medicinal ingredient.

Meaning of the term 'applied to teeth' used herein may include from immediately after locating the preparation of the present invention to teeth or tooth peripheries to before adhering the preparation to teeth by applying pressure by a user.

The term 'when adhering the preparation to teeth' in the present invention means the time of adhering the preparation to curves of teeth, interproximal space, or the boundary between teeth and gums by applying pressure after a certain period of time after application of the preparation to teeth.

The term 'time of removal of the preparation' in the present invention may mean the time that the drug is released from the oral cavity after it is adhered to teeth or tooth peripheries and then the preparation is removed therefrom. Depending on the purpose and use of the preparation, and the release amount of the drug, but it may be removed after 2 hr from attachment, but it may be removed within 30 min, more preferably within 10 min after adhered to teeth in view of convenience of use. Hardness of the preparation at the time of removal may be increased, compared to the time at which the preparation is applied to teeth and the time at which the preparation is adhered to teeth, and hardness of the preparation at the time of removal may be increased.

The term 'controlling phase transition rate' used herein can be used in the same sense as controlling the hardening rate and hardening degree of the preparation, and means that the hardening degree of the preparation can be controlled by phase transition with time.

The present inventors have studied on a drug delivery system capable of delivering a medicinal ingredient into the oral cavity, thereby suggesting a novel form of a drug delivery system and a novel method for delivering the medicinal ingredient into the oral cavity using such a system.

The present inventors have studied for a long time on a novel drug delivery system capable of effectively delivering a medicinal ingredient to specific sites in the oral cavity (for example, sites requiring tooth whitening, site of generation of sensitive teeth, sites of oral inflammation, sites of periodontal disease, etc.). As a result, a novel form of an oral preparation, which can be conveniently applied to teeth or a mucosal region in the oral cavity, and can be adhered well up to a curvy region and interproximal space so as to increase the drug reach rate at the desired site, has been developed.

Formulations, which are advantageous for delivering a drug up to interproximal space, have generally been recognized as liquid or highly flowable forms. However, the initial viscosity is so low that the formulations flow well and are not only inconvenient to use but also have a problem that sufficient contact time cannot be secured because the time to be adhered to the target site is short.

In order to solve this problem, the present inventors developed a formulation that is in a dough-like form and when it is attached to teeth or a target site in the oral cavity, it does not flow down well while increasing initial adhesive force. Furthermore, the present inventors confirmed that, in particular, when a polymer having strong adhesive property to gums and teeth in the oral cavity and having a property of being involved in phase transition mechanism is mixed with a phase transition compound, there is no large difference in viscosity between the time of the initial use and the time of removal, and therefore it can be easily attached and removed without any irritation, through tests, thereby developing a novel form of a preparation.

Meaning of the term 'applied to teeth' used may include from immediately after locating the preparation of the present invention to teeth or tooth peripheries to before adhering the preparation to teeth by applying pressure by a user.

The term 'when adhering the preparation to teeth' in the present invention means the time of adhering the preparation to curves of teeth, interproximal space, or the boundary between teeth and gums by applying pressure after a certain period of time after application of the preparation to teeth.

The term 'time of removal of the preparation' in the present invention may mean the time that the drug is released from the oral cavity after it is adhered to teeth or tooth peripheries and then the preparation is removed therefrom. Depending on the purpose and use of the preparation, and the release amount of the drug, but it may be removed after 2 hr from attachment, but it may be removed within 30 min, more preferably within 10 min after adhered to teeth in view of convenience of use. Hardness of the preparation at the time of removal may be increased, compared to the time at which the preparation is applied to teeth and the time at which the preparation is adhered to teeth, and hardness of the preparation at the time of removal may be increased.

In one embodiment of the present invention, the preparation of the present invention may comprise a polymer of controlling hardening rate of the phase transition compound. The preparation according to one embodiment of the present invention comprising the polymer of controlling hardening rate of the phase transition compound may have low initial hardness that is convenient for use and may have relatively low hardness at the time of removal after drug release is completed. Therefore, an oral preparation which can be easily removed and also less irritating to the attachment site can be provided.

For example, among phase transition compounds, in the case of alginate powder, when it is in contact with moisture, it hardens rapidly at the beginning and the hardness is increased significantly with time. Therefore, release of the medicinal ingredient dispersed in the preparation may not be smooth. However, in one embodiment of the present invention, a preparation prepared by mixing a polymer having a large number of carboxyl groups, which are the same reacting group as alginate, for example, PVM/MA (Gantrez) polymer is advantageous in releasing a drug without experiencing rapid hardness change.

The term 'hardness' used herein may mean the amount of force required to compress the preparation. Hardness of the preparation of the present invention is measured at compression test mode of Stable Micro System TA XT Plus. After filling 20 g of the preparation into a 50 mL beaker, a 20 mm diameter aluminum probe for hardness measurement is set, and then hardness is measured with test speed of 1.5 mm/s, distance as target mode and distance of 10 mm. Hardness is understood as the peak value of the first cycle calculated. The unit can be expressed as g (g force).

The phase transition compound is a substance that causes viscous property to the oral composition. It may be carrageenan, pectin, xyloglucan, gellan gum, ammonium alginate, magnesium alginate, potassium alginate, sodium alginate, lithium alginate, chitosan, poly-lactic acid (poly(D,L-lactic acid)), polylactide-co-glycolide (poly(DL-lactide-co-glycolide)), poly-caprolactone, polyacrylic acid (carbopol), polyvinylacetal diethyl aminoacetate (AEA), hydroxypropylmethyl cellulose, poly(methacrylic acid)-poly(ethylene glycol), poly(D,L-lactide)-block-poly(ethylene glycol)-block-poly(D,L-lactide), PEG-oligoglycolyl-acrylate, poly(N-isopropyl acrylamide), sucrose acetate isobutyrate, polyvinyl alcohol, polyvinyl acetate, glyceryl monooleate, glyceryl monolinoleate, glyceryl monoarachidonate, glyceryl monostearate and the like alone or a combination of two or more thereof. Any material that can be used as a phase transition compound in the art can be used and is not limited to the above examples.

Preferably, the phase transition compound may be ammonium alginate, magnesium alginate, potassium alginate, sodium alginate, lithium alginate or a mixture thereof.

The phase transition compound may be contained in the preparation together with a polymer having a property of controlling hardening rate of the phase transition compound. The polymer having a property of controlling hardening rate of the phase transition compound may have the same functional group (for example, carboxyl group) as the functional group contained in the phase transition compound.

The polymer having a property of controlling hardening rate of the phase transition compound contained in the preparation of the present invention may comprise at least one selected from polymers having a functional group involved in the phase transition mechanism of the phase transition compound such as carboxyl group, hydroxyl group and the like. For example, when the preparation of one embodiment of the present invention is subjected to phase transition reaction by alginic acid and a salt thereof, the polymer may be a polymer having a carboxyl group, for example, at least one polymer selected from the group consisting of polyacrylic acid, sodium polyacrylate, carbomer, carbopol, acrylate copolymer (Eudragit L-100), polyquarternium-39 and a copolymer of methyl vinyl ether and maleic anhydride (PVM/MA copolymer). Preferably, the polymer may be Gantrez that is one of copolymers of methyl vinyl ether and maleic anhydride, and most preferably, it may be Gantrez S-97 that is water-soluble and in a grade applicable to oral products. The polymer may be preferably used for the purpose of the present invention due to its excellent adhesive force to teeth and gums. On the contrary, when the preparation is subjected to phase transition reaction by polyvinyl alcohol, a polymer having a hydroxyl group, for example, at least one polymer selected from the group consisting of polyethylene glycol, hyaluronate, microcrystalline cellulose, hydroxypropyl methyl cellulose, methyl cellulose, alginic acid and carrageenan.

Although the polymer having a property of controlling hardening rate of the phase transition compound is believed to interfere with the binding of the phase transition compound to water-soluble calcium, and a carboxyl group (—COOH) contained therein interferes with the hardening of the phase transition compound by binding to the water-soluble calcium, the present invention is not to be construed as limited to such theory Preferably, the polymer having a property of controlling hardening rate of the phase transition compound may be water-soluble and also contain the same functional group as the functional group contained in the phase transition compound. For example, the —COOH group contained in PVM/MA binds to water-soluble calcium and interferes with the binding of alginate to the water-soluble calcium, thereby delaying hardening.

The polymer having a property of controlling phase transition reaction rate may be contained in an amount of 0.01 wt % to 10 wt % based on the total weight of the preparation, and preferably it may be contained in an amount of 0.05 wt % to 5 wt %. When it is in contact with water within the above range, the present invention can have the desired hardness range and can provide excellent adhesive force. Further, when the content ratio of the polymer exceeds the above range, the binding with the phase transition compound is strong enough to affect the release of the dispersed medicinal ingredient and inhibit the release of the medicinal ingredient. The phase transition compound and the polymer having a property of controlling phase transition reaction rate may be mixed at a weight ratio of 5:0.01 to 0.07, preferably 5:0.03 to 0.05 (phase transition compound: polymer having a property of controlling phase transition reaction rate). When the weight ratio is within the above weight ratio range, the desired hardness of the preparation can be achieved.

The medicinal ingredient can be homogeneously dispersed in the oral composition, and the case that the ingredient is inhomogeneously dispersed is also included in the mixing of the present invention.

According to one embodiment of the present invention, the preparation of the present invention has semi-solid property at the same time, so that it can be adhered to curves or gap.

The preparation of the present invention may have a form such as dough or clay, and it can be applied to teeth or tooth peripheries as the form of an ointment.

In one embodiment of the present invention, the preparation may be used as two-formulation type, and as needed, it may be used as three-formulation type. For example, i) the first formulation containing a phase transition compound; and the second formulation containing a polymer of controlling phase transition reaction rate, water, a medicinal ingredient and other ingredients which can be contained in a preparation may be mixed, and ii) the first formulation containing a phase transition compound; the second formulation containing a polymer of controlling phase transition reaction rate; and the third formulation containing water, a medicinal ingredient and other ingredients which can be contained in a preparation may be mixed.

The first formulation and the second formulation or the first formulation, the second formulation and the third formulation may be mixed and then applied to teeth or tooth peripheries.

According to another embodiment of the present invention, the present invention provides a preparation for attaching to teeth or tooth peripheries, which comprises: a phase transition compound; and a polymer which makes hardness of the preparation after 1 min from mixing with the phase transition compound 140 g to 350 g and makes hardness of the preparation after 10 min from the mixing with the phase transition compound 5,200 g to 13,000 g, and delivers the medicinal ingredient contained in the preparation into the oral cavity.

The phase transition compound may be any substance causing viscous property that is included herein without limitation, and preferably, it may be carrageenan, pectin, xyloglucan, gellan gum, ammonium alginate, magnesium alginate, potassium alginate, sodium alginate, lithium alginate, chitosan, poly-lactic acid (poly(D,L-lactic acid)), polylactide-co-glycolide (poly(DL-lactide-co-glycolide)), poly-caprolactone, polyacrylic acid (carbopol), polyvinylacetal diethyl aminoacetate (AEA), hydroxypropylmethyl cellulose, poly(methacrylic acid)-poly(ethylene glycol), poly(D,L-lactide)-block-poly(ethylene glycol)-block-poly(D,L-lactide), PEG-oligoglycolyl-acrylate, poly(N-isopropyl acrylamide), sucrose acetate isobutyrate, polyvinyl alcohol, polyvinyl acetate, glyceryl monooleate, glyceryl monolinoleate, glyceryl monoarachidonate, glyceryl monostearate and the like alone or a combination of two or more thereof. Any material that can be used as a phase transition compound in the art can be used and is not limited to the above examples. Preferably, the phase transition compound may be alginic acid or its salts, and preferably, the alginic acid or its salts may be ammonium alginate, magnesium alginate, potassium alginate, sodium alginate, lithium alginate or a mixture thereof.

For effective release of the medicinal ingredient contained in the preparation which comprises the phase transition compound and for effective adhesion to teeth, interproximal space or tooth peripheries, the preparation should have enough viscous property and hardness for easy handling of the preparation during 1 min after mixing the first formulation and the second formulation, and preferably, hardness of 140 g to 350 g may be good for easy handling. And after 10 min from the mixing of the ingredients of the preparation, the drug release may occur smoothly, and hardness of 5,200 g to 13,000 g may be good for maintaining shape fixing force and adhesive force. In order to provide the hardness of the preparation intended in the present invention, the preparation may preferably comprise at least one selected from the group consisting of polyacrylic acid, sodium polyacrylate, carbomer, carbopol, acrylate copolymer (Eudragit L-100), polyquarternium-39 and copolymer of copolymer of methyl vinyl ether and maleic anhydride (PVM/MA copolymer). Preferably, the polymer may be copolymer of methyl vinyl ether and maleic anhydride (PVM/MA copolymer).

The shape fixing force which can be achieved by the preparation of the present invention can secure sufficient contact time with the site where a drug is required to reach, and therefore, it may be more advantageous in achieving the desired effect.

The preparation according to one embodiment of the present invention may have difference between the hardness measured after 1 min from the mixing and the hardness measured after 10 min from the mixing may be 5,000 g to 12,000 g, preferably 6,000 g to 10,000 g. When the hardness difference is within the above range, attachment and handling may be easy, and also drug release may be effective and removal may be easy. Therefore, it may be more advantageous in achieving the purpose of the present invention.

The preparation of the present invention may further comprise a material for helping drug release. The material for helping drug release may be any material that can form a channel, a porous structure or bubble (foam) in the formulation. For example, in the case that the preparation is consisting of two formulations of the first formulation and the second formulation, one formulation contains an acid and the other contains a base, so that bubbles are formed in the formulation when the two formulations meet to form a viscous form. Namely, the first formulation contains acetic acid, lactic acid, malic acid, gluconic acid, ascorbic acid and the like or a water-soluble salt thereof, e.g., sodium citrate, and the second formulation contains at least one base selected from the group consisting of sodium hydroxide (NaOH), potassium hydroxide (KOH), sodium bicarbonate (baking soda) and sodium carbonate. Preferably, the acid may be acetic acid, and the base may be sodium carbonate, and more preferably, those may be sodium citrate and sodium bicarbonate, which are an acid and a base mainly used in a toothpaste.

The hardness of the preparation of the present invention is gradually increased as the phase transition compound comes into contact with moisture by mixing the first formulation and the second formulation. Therefore, it is easy to be attached to teeth and may not cause any irritation to teeth or gums at the time of removal because it has lower hardness at the time of removal than the hardness range at the time that a typical phase transition compound and water meet and has shape fixing force.

The preparation for attaching to teeth or tooth peripheries provided in another embodiment of the present invention comprises: i) a medicinal ingredient, ii) a phase transition compound, and iii) a polymer that is water-insoluble but ethanol-soluble. The preparation of the present invention is applied in liquid to teeth or tooth peripheries, and then phase transited by contacting with saliva in the oral cavity, thereby having adhesiveness to teeth or tooth peripheries. Therefore, it may have adhesive property to teeth or tooth peripheries.

Ethanol is used as a solvent for manufacturing the preparation. The preparation of the present invention contains a polymer that is not dissolved in water at all or dissolved in water only in a certain condition (for example, at a certain ratio of water and ethanol (for example, ethanol is contained in an amount of 80% or more in a mixture of water and ethanol) or at a certain pH condition), but dissolved in ethanol. The preparation may contain a polymer that is water-insoluble but ethanol-soluble. The polymer that is water-insoluble but ethanol-soluble may include a polymer that is not dissolved in water but dissolved in ethanol in conditions of a temperature of 35° C. to 38° C., pH 7.

The preparation may provide excellent spreadability when applied to teeth or tooth peripheries, and may have adhesive property to teeth or tooth peripheries after a certain period of time in the oral cavity.

The inventors of the present invention confirmed through tests that the ingredients contained in the preparation induce phase transition by contacting with saliva, and at the same time, a polymer that is water-insoluble but ethanol-soluble is used together, so that even if a large amount of the preparation is loaded and thickly applied to the target site, the preparation can quickly harden and may have adhesive property for enough time.

Solubility of the preparation of the present invention is changed in the humid oral cavity. Namely, the preparation is dissolved in ethanol, which is a solvent of the preparation, and the solubility is reduced while being in contact with a large amount of water (saliva) having pH of 7 or lower in the oral cavity, and can remain at the target site for enough time to achieve the desired effect.

The preparation of the present invention is in the form of liquid having excellent flowability immediately after application in the oral cavity, and can penetrate well into the interproximal space and the boundary between teeth/gums. The preparation of the present invention reacts with saliva over time after application, so that the preparation hardens gradually and goes through gelation. Therefore, the preparation can be attached to teeth or tooth peripheries.

The term "gelation" does not only include the phenomenon that the sol changes into gel, but also includes phenomenon accompanied by a pronounced increase in elasticity or viscosity of the system. It includes a phenomenon in which the liquid phase gradually solidifies in contact with saliva, and there is no particular limitation on the degree to which the elasticity or viscosity is increased by gelation.

The phase transition compound may include any one monoglyceride selected from glyceryl monooleate, glyceryl monolinoleate, glyceryl monoarachidonate, glyceryl monostearate or a mixture thereof, and preferably, it may be glyceryl monooleate and/or glyceryl monolinoleate.

The phase transition compound is preferably glyceryl monooleate for the purpose of the present invention to induce phase transition in contact with moisture. The phase transition compound can be contained in an amount of 5 wt % to 80 wt % based on the total weight of the preparation. It is preferable for the purpose of the present invention to have a feature of phase transition upon contact with a small amount of water or saliva in the above content range.

The preparation of the present invention uses a polymer that is dissolved only in ethanol and hardly dissolved in water together, and the polymer dissolved only in ethanol is also converted from soluble phase into insoluble phase upon contact with water. Therefore, since the polymer dissolved only in ethanol goes through phase transition in a different sense, the phase transition compound may be included in the preparation in such a content range.

The polymer that is water-insoluble but ethanol-soluble, contained in one embodiment of the present invention, may include a) a polymer that is dissolved in ethanol but not dissolved in water, or b) a polymer that is dissolved in ethanol but not normally dissolved in water but dissolved in water in a certain condition such as pH higher than the pH in the oral cavity (pH 7), for example a typical enteric coating polymers that is not dissolved in the stomach which is an acidic condition, in the formulation which is a neutral condition but dissolved only in the intestine which is a basic condition. For example, b) the polymer that is not normally dissolved in water but dissolved in water in a certain condition such as pH higher than the general pH in the oral cavity (pH 7) may include a polymer that is dissolved in ethanol but not dissolved in water having pH of 7 or lower.

Monoglyceride is characterized in that it is phase transited depending on the temperature and moisture content, and has a characteristic of changing the structural form and physical properties as the phase changes. When the monoglyceride shows phase transition, it is converted from the structure having fluidity into the structure having adhesive property without fluidity. However, because the monoglyceride should be applied thickly to make fast phase transition, it was characterized that the monoglyceride is applied to the desired target as a spray type as thin as possible. The phase transition preparation using the monoglyceride was too thin to be sufficient for delivery of a sufficient amount of a drug, and only partially used in preparations that did not require drug delivery with sufficient attachment time, such as some bad breath removers.

The present invention solves these problems and suggests a method for effectively delivering a drug while securing sufficient attachment time.

The polymer that is water-insoluble but ethanol-soluble may be ethyl cellulose, butyl ester of PVM/MA copolymer, polyvinyl acetate, polyvinyl acetate-phthalate, shellac, rosin, methacrylic acid copolymer (for example, EUDRAGIT® L100, L100-55) or a mixture thereof, and preferably, it may be ethyl cellulose, butyl ester of PVM/MA copolymer or a mixture thereof.

In one embodiment of the present invention, in particular, the medicinal ingredient may preferably be a medicinal ingredient that is not dissolved in water well but dissolved only in ethanol. In another embodiment, the medicinal ingredient may preferably be a medicinal ingredient that is not dissolved in water well but homogeneously dispersed in water.

The preparation according to another embodiment of the present invention may typically have viscous property similar to viscous property of the flowing solution or gel, and for example, it may have viscous property of 10,000 or less, preferably 5,000 or less, more preferably 100 to 10,000, most preferably 500 to 5,000 when measured at room temperature by Brookfield Viscometer with RV6 spindle at speed 20. Through Examples, the present invention provides a preparation for attaching to teeth or tooth peripheries, which has the viscosity of the above range before contacting with saliva, but is phase transited to gel or solid having adhesive property to teeth or oral tissues after applied to teeth or in the oral cavity. The phase transition can be measured at an oral temperature condition, preferably at a temperature of 36° C. to 38° C.

The viscous property can be obtained as a result of measuring the viscosity using Brookfield viscometer commonly used in the art at a condition of RV6 spindle at room temperature or oral temperature, and the viscous property refers to a property having viscous property, and the viscous property and the viscosity may be used interchangeably. The unit may be expressed as cPs.

The preparation may comprise the polymer that is water-insoluble but ethanol-soluble and the phase transition compound of the present invention.

In one embodiment, the preparation may comprise both of a polymer selected from glyceryl monooleate, glyceryl monolinoleate, glyceryl monoarachidonate, glyceryl monostearate or a mixture thereof; and a polymer selected from ethyl cellulose, butyl ester of PVM/MA copolymer, polyvinyl acetate, polyvinyl acetate-phthalate, shellac, rosin, methacrylic acid copolymer or a mixture thereof.

The term 'tooth peripheries' used herein is generally a concept involving a region represented by gums, and may be used to mean including all of the mucosal regions around teeth. The surrounding part of teeth can be used to mean covering the region where a medicinal ingredient for intra-oral delivery can be delivered together with the teeth when the preparation is applied to the teeth in the structure of the preparation. Herein, 'teeth or tooth peripheries' is used together with 'teeth', and it may be understood herein to include both the teeth and the tooth peripheries even if it is described only as 'teeth.

The term 'preparation' used herein means to a product made by processing the medicinal ingredient to secure its therapeutic effect without affecting effectiveness of the medicinal ingredient.

The meaning 'applied to teeth' used herein may be included in the meaning of application when the preparation of the present invention is brought into contact with teeth or a part of tooth peripheries.

The present inventors have studied on a drug delivery system capable of delivering a medicinal ingredient into the oral cavity, thereby suggesting a novel form of a drug delivery system and a novel method for delivering the medicinal ingredient into the oral cavity using such a system.

The preparation may further comprise a backing layer as required when it is attached to teeth or tooth peripheries. The preparation according to one embodiment of the present invention may be smeared to unwanted portions such as gums if the preparation hardens for a long time. Thus, the backing layer may also prevent the problem. The backing layer may include a water-insoluble polymer, generally used in an oral film, and for example, polyethylene (PE), polypropylene (PP), ethylene vinyl acetate (EVA), cellulose acetate phthalate, shellac, polyvinyl acetate, ethyl cellulose, polymethyl methacrylate, methacryloylethyl betain/methacrylate copolymer (Yukaformer; Manufacturer: Mitsubishi), methacrylic acid copolymer (Eudragit L 100, Eudragit L 12,5, Eudragit L 100-55, Eudragit L 30D-55), aminoalkyl methacrylate copolymer (Eudragit E 100, Eudragit E 12,5, Eudragit RL 100, Eudragit RL 30D) and the like may be used.

The preparation according to one embodiment of the present invention may be easily removed by tooth brushing at the time of removal after drug release is completed.

According to one example of use, after applying the dough-type preparation of the present invention on the backing layer, the baking layer is attached to the target site in the oral cavity, and then the backing layer may be removed after a certain period of time (when the preparation somewhat hardens and is not smeared to gums and the like). After removing the backing layer, the preparation of the present invention can be removed by tooth brushing with a tooth brush usually used at the time of removal. When used in a peel-off type, the backing layer can be removed at the time of removal together with the preparation without removing the backing layer in the middle of the hardening process.

For example, the preparation of the present invention can be removed by brush-off (by tooth brushing) at the time of removal from teeth or tooth peripheries after a certain period of time. The preparation of the present invention can be detached by external stimulation or pressure such as normal tooth brushing. A tool for brush-off may be, for example, a toothbrush, a sponge and the like, but the kind is not particularly limited.

Advantageous Effects

The preparation of the present invention can give high adhesive force to the desired site despite interproximal space or curves of teeth.

The preparation of the present invention can be easily removed without leaving stickiness on the tooth surfaces at the time of removal.

The preparation of the present invention is excellent in agglomeration, which can be self-healed like gum or dough. It is also easy to handle while controlling drug release.

The preparation is possible to sufficiently secure contact time between the drug delivery site and the preparation of the present invention because the preparation does not flow down or is not diluted with saliva after attachment, and therefore, it is advantageous to achieve the desired efficacy.

The preparation can be used conveniently because it does not flow down when applied to teeth.

The preparation has a relatively high hardness at the beginning of attachment, so that it can be easily handled without flowing down, and it can be easily removed and may cause less irritation around the attached site due to its relatively small increase in hardness after a certain period of time from the attachment.

In general, oral preparations containing phase transition compounds should be applied to a thickness that is too thin to secure sufficient contact time with the attachment site, but the present invention can secure sufficient contact time because solubility of the preparation is rapidly changed (soluble→insoluble) in the humid oral cavity even if the preparation is applied thickly.

Figure 1:
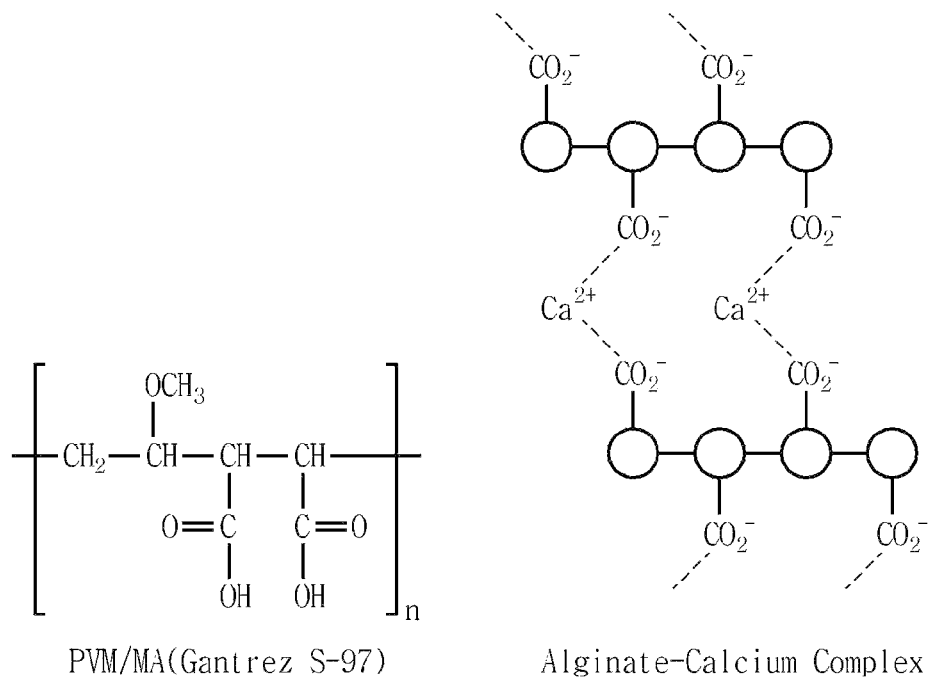
FIG. 1 shows PVM/MA that is an example of a polymer which can control hardening rate of a phase transition compound according to the present invention (left), and illustrates structure of the formed alginate-calcium complex (right).

T refers to teeth, and 10 refers to a preparation for attaching to teeth or tooth peripheries.

DETAILED DESCRIPTION OF INVENTION

Hereinafter, the present invention will be described in more detail through the following embodiments. However, the embodiments according to the present invention may be modified in many different forms, and the scope of the present invention shall not be construed as being limited to the embodiments described below. The embodiments of the present invention are provided for illustration to help a full understanding of the present invention. Unless stated otherwise, % used herein is understood to mean wt %.

EXAMPLES

[Preparation of Mouth Band and Oral Preparation]

Examples and Comparative Examples were manufactured according to the following method.

The preparations were manufactured according to the following composition by adjusting to 50° C. and then mixing with a mechanical mixer.

TABLE 1

| Example 1 | | Example 2 | | Example 3 | |
|---|---|---|---|---|---|
| PVA | 2.8% | PVA | 2.8% | PVA | 2.8% |
| Magnoliae Cortex extract | 0.05% | Centella extract | 0.02% | Zinc chloride | 0.1% |
| ethanol | 1.0% | ethanol | 1.0% | TPP | 10.0% |
| Borax | 1.2% | Borax | 1.2% | Aerosil200 | 1.2% |
| Sodium Alginate | 0.3% | Aerosil200 | 2.4% | Water | to 100% |
| Water | to 100% | Water | to 100% | | |

TABLE 2

| Comparative Example 1 | | Comparative Example 2 | | Comparative Example 3 | | Comparative Example 4 (P&G SensiStop ™) |
|---|---|---|---|---|---|---|
| PVA | 2.8% | PVA | 10% | PVA | 2.8% | Cellulose Gum. Carbomer, NaOH, Glycerin, Water |
| Magnoliae Cortex extract | 0.05% | Centella extract | 0.02% | Zinc chloride | 0.1% | |
| ethanol | 1.0% | ethanol | 1.0% | TPP | 10.0% | |
| Borax | 1.2% | Water | to 100% | Water | to 100% | |
| Water | to 100% | | | | | |

[Evaluation of Adhesive Force in Interproximal Space and Buccal Surface]

1. Test for Comparison of Interproximal Space and Buccal Surface Adhesive Force (Applying Method for Removing Artificial Dental Plaque)

(1) Test Method

Evaluation device: ITPlus 4.0 Microcam

Evaluation method: Before and after attachment of Comparative Examples and Examples, rate for removing artificial dental plaque on interproximal space and buccal surface was compared by area a) Method for Coating Artificial Dental Plaque on Artificial Dental Model Among gnathostaic models, maxillary posterior buccal surface that is easy to apply a troothbrush was inserted into a polymer (containing Red Dye) for 10 sec. After removing it, it was dried at room temperature for 60 min and then dried again in a drying room for 60 min to manufacture artificial dental plaque.

b) Test Method for Interproximal Space and Buccal Surface Adhesive Force

Examples and Comparative Examples were sprayed with a small amount of water to adjust the humid oral conditions and then adhered to the artificial dental plaque coated artificial teeth to be tested. Then, the artificial dental plaque on the interproximal space and the frontal surface of the tooth was removed by removing the preparation after 10 min under the same conditions, and then area of the interproximal space and the buccal surface was measured and compared.

(2) Test Result

The area of the artificial dental plaque removed from the interproximal space and the frontal surface by the use of Example and Comparative Example was measured. (The large area of plaque removal reflects the high adhesive force at that location)

TABLE 3

| Area | Example 1 | Example 2 | Comparative Example 1 | Comparative Example 4 |
|---|---|---|---|---|
| Interproximal space | 30.01 | 28.90 | 25.80 | 10.55 |
| Buccal surface | 89.98 | 85.33 | 79.12 | 70.11 |

As can be seen from Table 3, Examples 1 and 2 showed large area of plaque removal at both of the interproximal space and the buccal surface. From the above result, it can be found that Examples 1 and 2 have excellent ability to be adhered up to the interproximal space, and it also can be found that those have low flowability and can secure sufficient contact time with the buccal surface, thereby having excellent ability to remove plaque from the buccal surface.

[Test for Comparison of Shape Retention Force and Length Extendibility]

1. Shape Retention Force

After attaching Example and Comparative Example to the dental model consisting of both the upper jaw and the lower jaw, the time at which shape was not maintained and the preparation began to flow was recorded to evaluate whether there is physical strength to maintain the attached shape during use time. Using the dental model, the preparation was attached to the maxillary area to cover about three or more boundary areas between gums and teeth. After 10 min, whether the preparation flows down to the mandibular area or maintains the attachment state was observed. Then, using 5-point scale, if the shape is maintained same as initial stage, it is marked as 5 point, if the preparation slightly flows down but the shape and the position are maintained, it is marked as 4 point, if the shape and the position are slightly off while flowing down, it is marked as 3 point, if the shape and the position are much off, it is marked as 2 point, and if the shape and the position are completely off from the attachment site, it is marked as 1 point.

TABLE 4

|  | Exam. 1 | Exam. 2 | Exam. 3 | Comp. Exam. 1 | Comp. Exam. 2 | Comp. Exam. 3 | Comp. Exam. 4 |
|---|---|---|---|---|---|---|---|
| Shape retention force | 5 | 5 | 5 | 3 | 2 | 2 | 4 |

2. Test for Comparison of Stretchable and Malleable Properties

For Examples showed excellent shape retention force in Table 4, length extendibility was further tested.

1 g of Example was taken and placed on a PET sheet in the size of 1 cm*1 cm, another PET sheet was placed thereon, and then the length that could be maximally extended without tearing or puncturing the sheet by pressing with a finger was measured and compared.

TABLE 5

|  | Example 1 | Example 2 | Example 3 | Comparative Example 4 |
|---|---|---|---|---|
| Extended length | 6 times | 8 times | 1.5 times | Not extended when pressed in product state |

As can be seen from Table 5, it can be found that Examples attached to the tooth surfaces have excellent shape retention force and excellent length extendibility, and therefore those have stretchable characteristic. In particular, Comparative Example 4 didn't show significant difference from Examples of the present invention in terms of shape retention force, but it had a characteristic in which the length was not extended when pressed. Due to this difference, the preparation of Comparative Example 4 was difficult to be completely adhered up to the interproximal space. However, the preparation of the present invention was able to have perfect adhesive force in consideration of curves or gaps of teeth.

[Survey for Convenience of Use to Human Subject (Adhesive Force, Shape Retention Force, Adhesive Force, Removability and the like)]

1) Test subject and instructions: A total of 10 volunteers were asked to use Examples 1 to 3 and Comparative Examples 1 to 4 alternately three times, respectively, and then survey was conducted using 5-point Likert scale.

2) Criteria
5: Very satisfied
4: Relatively satisfied
3: Moderate
2: Little unsatisfied
1: A lot unsatisfied As guideline, if the preparation was easily attached to the desired position and stuck to the place for the desired time where it was attached, the adhesive force was evaluated to be excellent, if the preparation was attached to the desired position and then it maintained the shape well without flowing down, the shape retention force was evaluated to be excellent, and if the preparation was easily adhered to the interproximal space or the boundary between teeth and gums by lightly pressing it with a finger, the adhesive force was evaluated to be excellent. Then, survey for removability was conducted according to the following 5-point Likert scale.

5 : Removal is very convenient and there is no residue on teeth.
4 : Removal is convenient but there is little residue.
3 : Removal is inconvenient and there is inconvenience due to residue.
2 : Removal is inconvenient and there are many residues.
1 : Removal is very inconvenient and there are so many residues.

3) Test Result

TABLE 6

|  | Exam. 1 | Exam. 2 | Exam. 3 | Comp. Example 1 | Comp. Example 2 | Comp. Example 3 | Comp. Example 4 |
|---|---|---|---|---|---|---|---|
| Adhesive force | 4 | 4 | 4 | 4 | 4 | 2 | 2 |
| Shape retention force | 5 | 5 | 5 | 3 | 2 | 2 | 4 |
| Adhesive force | 5 | 5 | 5 | 5 | 2 | 5 | 3 |
| Removability | 5 | 5 | 5 | 4 | 2 | 4 | 2 |

As can be seen from Table 6, Examples were able to obtain very excellent results overall in terms of adhesive force. Namely, the degree of flowing down after attachment was less than that of Comparative Examples.

Further, Examples obtained good result in terms of adhesive force, but when considering the shape retention or adhesive force overall, Examples obtained more excellent sense of use result.

[Survey for Clinical Sensitive Teeth or Gingivitis Relief to Human Subject]

1) Test subject and instructions: Examples 1 to 3 and Comparative Examples 1 to 4 were attached to sensitive teeth or gum pain area for 10 min once a day and then removed.

2) For each group, 15 volunteers who experienced sensitive teeth or gum pain were asked to use for 1 week and then survey was conducted according 5-point Likert scale.

5: Sensitive teeth/gum pain relief effect lasted for one month in all attached sensitive teeth/gum pain areas.
4: Sensitive teeth/gum pain relief effect was definitely felt in all attached sensitive teeth/gum pain areas.
3: Sensitive teeth/gum pain relief effect was definitely felt in at least one attached sensitive teeth/gum pain area.
2: Sensitive teeth against cold food or gum pain after eating became less sensitive, compared to before use.
1: Sensitive teeth or gum pain relief effect was not felt.

The survey results of efficacy of Example and Comparative Example were obtained as follows.

TABLE 7

|  | Exam. 1 | Exam. 2 | Exam. 3 | Comp. Example 1 | Comp. Example 2 | Comp. Example 3 | Comp. Example 4 |
|---|---|---|---|---|---|---|---|
| Sensitive teeth relief | — | — | 4 | — | — | 3 | 3 |
| Gingivitis relief | 4 | 4 | — | 3 | 1 | — | — |

As can be seen from Table 7, mouth bands of Examples showed more excellent efficacy in the oral cavity than those of Comparative Examples. Mouth bands of Examples had excellent adhesive force to the target site in the oral cavity and could deliver the drug up to the interproximal space. Therefore, those are advantageous to achieve the desired effect. Further, sufficient contact time could be secured and therefore drug delivery was easy.

[Preparation of Oral Preparation]

Oral preparations of Examples and Comparative Examples having the following composition were manufactured or purchased.

Examples and Comparative Examples were manufactured according to the following method.

The preparations were manufactured according to the following composition by adjusting the temperature of the second formulation to 50° C. and then mixing with a mechanical mixer. The amount of the alginate powder mixed with the second formulation was 100 times to the weight of the second formulation.

TABLE 8

|  | Example 4 | | Example 5 | | Example 6 | |
|---|---|---|---|---|---|---|
| First formulation | Alginate powder | | Alginate powder | | Alginate powder | |
| Second formulation | Zinc chloride (medicinal ingredient) | 2.0% | Magnoliae Cortex extract (medicinal ingredient) | 0.1% | Hydrogen peroxide (medicinal ingredient) | 6.0% |
|  | PVM/MA | 0.2% | PVM/MA | 0.35% | PVM/MA | 1.0% |
|  | Water | to 100% | Water | to 100% | Water | to 100% |

|  | Comparative Example 5 | | Comparative Example 6 | | Comparative Example 7 | |
|---|---|---|---|---|---|---|
| First formulation | Alginate powder | | Alginate powder | | Alginate powder | |
| Second formulation | Zinc chloride (medicinal ingredient) | 2.0% | Magnoliae Cortex extract (medicinal ingredient) | 0.1% | Hydrogen peroxide (medicinal ingredient) | 6.0% |
|  | Water | to 100% | PVA | 0.35% | HPMC | 1.0% |
|  |  |  | Water | to 100% | Water | to 100% |

[Hardness Comparison Test (Test Method: Measured by Using Texture Analyzer)]

Evaluation device: Stable Micro System TA XT Plus

Evaluation method: Hardness of Comparative Example and Example was measured by using Texture Analyzer Hardness was measured at compression test mode of TA (Texture Analyzer). After filling 20 g of Example and Comparative Example into a 50 mL beaker, a 20 mm diameter aluminum probe for hardness measurement was set, and then hardness was measured with test speed of 1.5 mm/s, distance as target mode and distance of 10 mm. The hardness calculated from the device is the peak value of the first cycle.

Test Result

The first formulations and the second formulations of Examples and Comparative Examples listed in Table 8 were mixed and then the results of comparison of hardness with time were shown in the following Table 9.

TABLE 9

|  | Example 4 | Example 5 | Example 6 | Comp. Example 5 | Comp. Example 6 | Comp. Example 7 |
| --- | --- | --- | --- | --- | --- | --- |
| 1 min from mixing | 150 g | 180 g | 340 g | 109 g | 120 g | 80 g |
| 3 min | 260 g | 280 g | 810 g | 14,800 g | 180 g | 15,000 g |
| 5 min | 2,400 g | 1600 g | 2,100 g | 21700 g | 5,000 g | 20,000 g |
| 10 min | 12,000 g | 5,600 g | 5,400 g | 22600 g | 16,000 g | 22,400 g |

Figure 2:
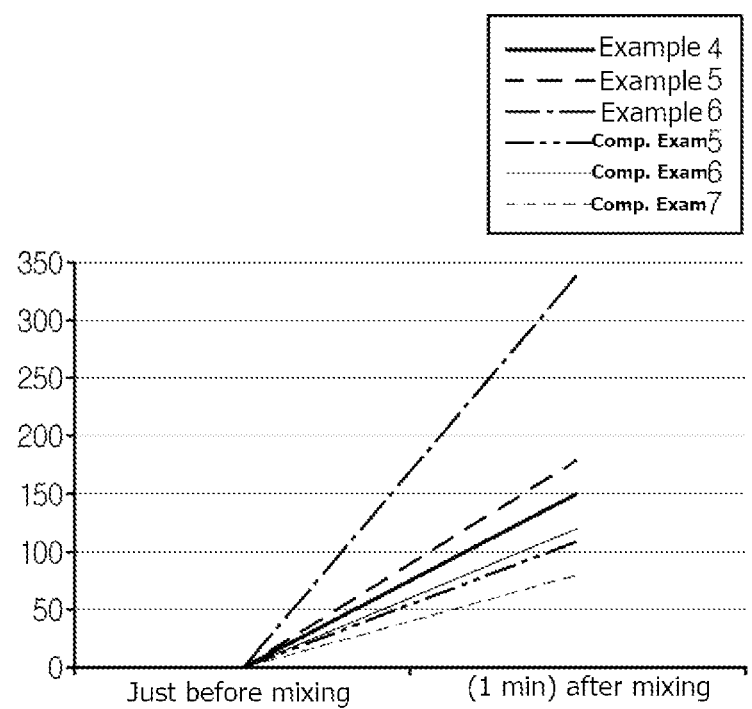
FIG. 2 shows hardness change checked after 1 min from mixing of the preparation. The unit of the vertical axis is denoted by g. As can be seen from FIG. 2, it can be found that in the case of Examples, harness is more rapidly increased from right after mixing the preparation to after 1 min from the mixing, and after 1 min from the mixing, hardness of Examples is higher than that of Comparative Examples. Namely, it can be confirmed that after 1 min from the mixing, the preparations of Examples are easier for users to handle than those of Comparative Examples.
Figure 3:
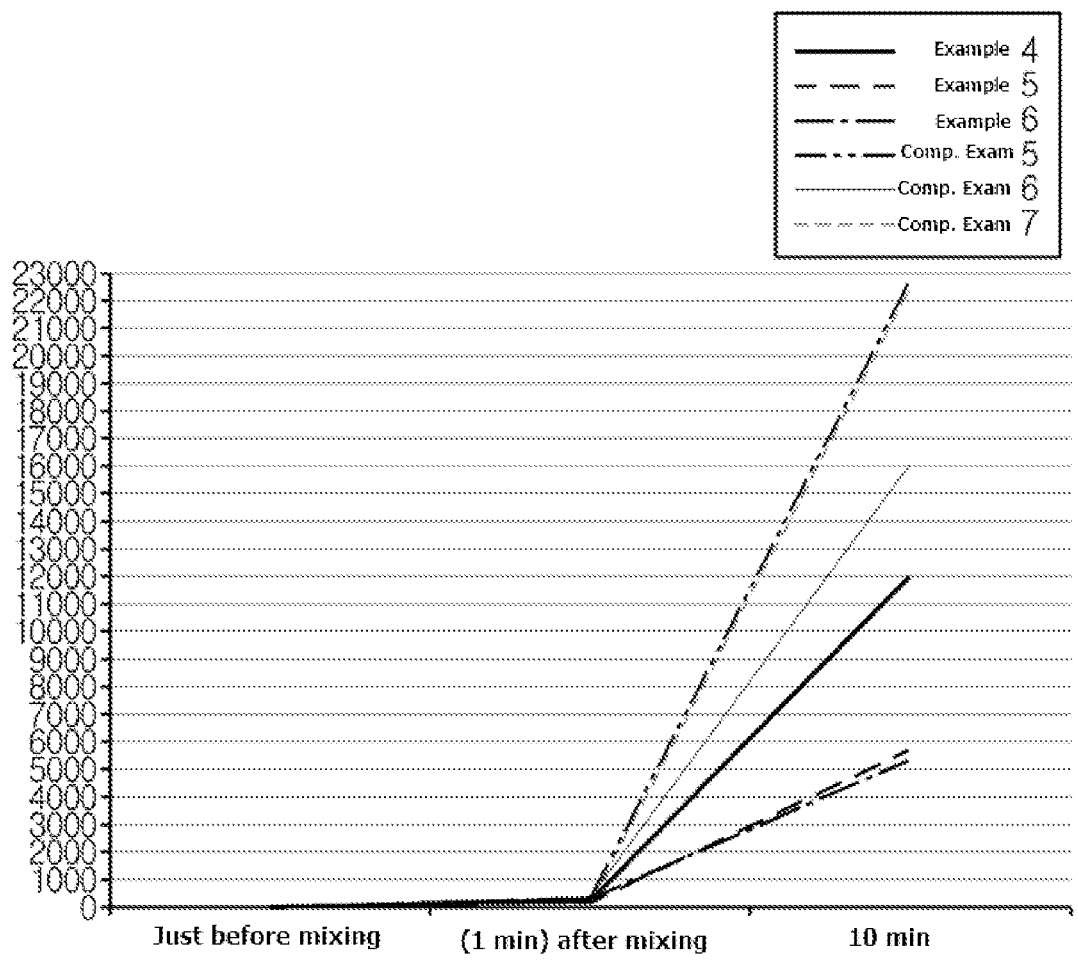
FIG. 3 show hardness change checked from just before mixing to after 10 min from the mixing. As can be seen from FIG. 3, it can be found that after 10 min from mixing, hardness of the preparations of Examples is lower than that of Comparative Examples. Namely, it can be found that Comparative Examples harden harder after a certain period of time from the attachment.
Figure 4:
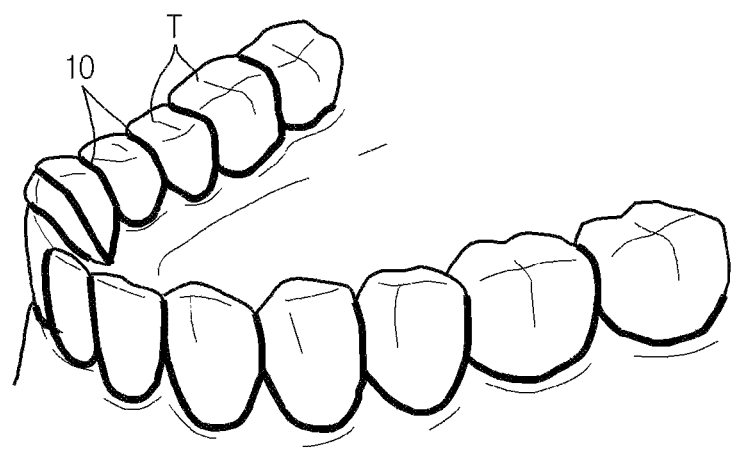
FIG. 4 is a drawing prefiguratively showing the process that the preparation according to one embodiment of the present invention is hardening after applying and adhering the preparation to teeth. As can be seen from FIG. 4, the preparation of the present invention can reach up to interproximal space.

As can be seen from Table 9, in the initial stage after mixing, the hardness values of Examples were higher and it was easy to apply to teeth or to be handled easily, and until 10 min after mixing, there was no large hardness change, so it was convenient to remove and easy to use without any irritation. The results of graphically representing the hardness change according to Examples and Comparative Examples were shown in FIG. 2 and FIG. 3.

[Test for Sense of Use after Attachment]

Test for sense of use was carried out using the preparations having the composition according to Table 8. The first formulation and the second formulation were mixed just before use, and then the mixture was applied on a backing layer. The preparation was attached to the desired site using the backing layer and then pressed with a finger to be adhered. It is not necessary to remove the backing layer, but in the test, the backing layer was removed after 2 min from the attachment. After 10 min from the attachment, the preparation was removed.

1. Survey for Adhesive Force

30 Respondents were asked to use each of the preparations of Comparative Examples 5 to 7 and Examples 4 to 6 depending on the group according to the above instructions. Then, each group changed and used the products and then responded to a questionnaire for adhesive force to gaps between teeth (interproximal space).

Criteria for Survey Response

5: Adhered well to gums and gaps between teeth by lightly pressing with a finger and easily removed 4: Adhered to gaps between teeth by lightly pressing with a finger but adhesive force to gums is moderate.

3: Adhered to gaps between teeth by lightly pressing with a finger but adhesive force to gums is weak.

2: Adhesive force to teeth is strong, but adhesive force to gaps between teeth is weak.

1: Adhesive force to teeth is strong, but adhesive force to gums is weak.

2. Survey for Removability

30 Respondents per group were asked to use each of the preparations of Comparative Examples 5 to 7 and Examples 4 to 6 according to the above instructions. Then, each group changed and used the products and then responded to a questionnaire for removability.

Criteria for Survey Response

5: Removal is very convenient and there is no residue on teeth.

4: Removal is convenient but there is little residue.

3: Removal is inconvenient and there is inconvenience due to residue.

2: Removal is inconvenient and there are many residues.

1: Removal is very inconvenient and there are so many residues.

3. Survey for Clinical Sensitive Teeth or Gum Pain Relief to Human Subject

1) Test subject and instructions: Example 5 and Comparative Example 1 were attached to sensitive teeth or gum pain area for 10 min once a day and then removed.

2) For each group, 15 volunteers who experienced sensitive teeth or gum pain were asked to use for 1 week and then survey was conducted according 5-point Likert scale.

3) Scale Criteria

5: Sensitive teeth or gum pain relief effect lasted for one month in all attached sensitive teeth or gum pain areas.

4: Sensitive teeth or gum pain relief effect was definitely felt in all attached sensitive teeth or gum pain areas.

3: Sensitive teeth or gum pain relief effect was definitely felt in at least one attached sensitive teeth or gum pain area.

2: Sensitive teeth against cold food was felt less sensitive, or gum pain was felt reduced, compared to before use.

1: Sensitive teeth or gum pain relief effect was not felt.

4. Survey for Feeling of Whitening Effect to Human Subject

1) Test subject and instructions: Examples 1 and 4 and Comparative Example 2 were attached to six teeth in the middle of the upper teeth for 30 min or longer once a day and then removed.

2) For each group, 15 volunteers who felt the need for tooth whitening because they usually thinks that their teeth are yellow were asked to use for 1 week. Then, survey for feeling of whitening effect, compared to the unattached lower teeth, was conducted according 5-point Likert scale.

3) Scale Criteria

5: Compared to the unattached lower teeth, felt a definite whitening effect than before use within 5 days.

4: Compared to the unattached lower teeth, felt that the teeth are definitely brighter than before use within 5 days.

3: Compared to the unattached lower teeth, felt that the teeth are definitely brighter than before use after 1 week use.

2: Compared to the unattached lower teeth, felt that the teeth are slightly brighter than before use.
1: Felt no difference, compared to before use.

5. Measurement Result

The following Table 10 shows removability and adhesive force of Comparative Examples and Examples, and sensitive teeth relieving effect, gingivitis relieving effect and degree of feeling of whitening were listed in table.

TABLE 10

|  | Exam. 4 | Exam. 5 | Exam. 6 | Comp. Exam. 5 | Comp. Exam. 6 | Comp. Exam. 7 |
| --- | --- | --- | --- | --- | --- | --- |
| Removability | 5 (peel-off) | 5 (brush-off) | 5 (brush-off) | 5 (peel-off) | 5 (peel-off) | 5 (peel-off) |
| Adhesive force | 5 | 5 | 5 | 5 | 5 | 5 |
| Sensitive teeth relieving effect | 4 | — | — | 2 | — | — |
| Gingivitis relieving effect | — | 5 | — | — | 2 | — |
| Feeling of whitening effect | — | — | 4 | — | — | 1 |

[Drug Release Rate Comparison Test]

A) Manipulation 0.9% Sodium chloride solution 500 mL is poured in a test tube and a temperature of a test solution is maintained at 32±0.5° C. during drug release test. Example or Comparative Example as a sample is fixed on the upper side of a disk which can be used as a sinker without absorbing, interfering or reacting so that a target attachment surface faces outward. Then, the disk is placed in the test tube with the sample-attached side facing up, and drug release time is calculated from this point of time. The sample-attached disk is aligned parallel to the bottom of the test tube and a paddle blade. Distance between the paddle blade and the sample surface is set to 25±2 mm, and revolutions per min (rpm) is set to 25.

At the time of sampling, 100 mL of sample solution is collected at a fixed position (a position 1 cm away from the wall of the test tube, between the top of the paddle blade and the test liquid surface) 30 min after the start of the test. The drug release test was conducted under a general laboratory condition, i.e., under a condition of relative humidity of about 65%, 25° C.

B) Drug Analysis Method

Depending on the drug or the content, an appropriate analysis is selected. For example, peroxides are analyzed by titration, metal salts are analyzed by ICP analysis, and natural extracts are analyzed by HPLC.

C) Result of Medicinal Ingredient Release Test

TABLE 11

|  | Exam. 4 | Exam. 5 | Exam. 6 | Comp. Exam. 5 | Comp. Exam. 6 | Comp. Exam. 7 |
| --- | --- | --- | --- | --- | --- | --- |
| Time for releasing 70% or more of medicinal ingredient | 10 min | 10 min | 10 min | Undetectable | Undetectable | Undetectable |

As can be seen from Table 11, it was confirmed that Examples could release about 70% of the medicinal ingredient at the time after 10 min from the attachment. However, in the case of Comparative Examples, drug release was not smooth due to rapidly increased hardness, and due to this, the degree of drug release was undetectable.

[Preparation of Oral Preparation]

Oral preparations of Examples and Comparative Examples having the following composition were manufactured or purchased.

TABLE 12

|  | Example 7 | | Example 8 | | Example 9 | |
|---|---|---|---|---|---|---|
| Composition | Vitamin E | 0.1% | Hydrogen peroxide | 6% | Oxalic acid | 6% |
|  | Magnoliae Cortex extract | 0.05% | Glyceryl monostearate | 30% | Glyceryl monolinoleate | 40% |
|  | Glyceryl monooleate | 41.5% | Ethyl cellulose | 10% | Butyl ester of | 8% |
|  | Ethyl cellulose | 8% | ethanol | to 100% | PVM/MA copolymer(50%) |  |
|  | ethanol | to 100% |  |  | ethanol | to 100% |

|  | Comparative Example 8 | | Comparative Example 9 | | Comparative Example 10 | |
|---|---|---|---|---|---|---|
| Composition | Vitamin E | 0.1% | Hydrogen peroxide | 6% | Oxalic acid | 2% |
|  | Magnoliae Cortex extract | 0.05% | Glyceryl monostearate | 30% | Butyl ester of | 8% |
|  | Glyceryl monooleate | 41.5% | Polyvinyl pyrrolidone | 2% | PVM/MA copolymer(50%) |  |
|  | ethanol | to 100% | ethanol | to 100% | ethanol | to 100% |

Comparative Example 11: Parodontax™

Comparative Example 12: Median intensive whitening gel (polyvinyl pyrrolidone, ethanol, water etc.)

Comparative Example 13: P&G Sensi Stop™

Examples and Comparative Examples of Table 12 were manufactured according to the following method.

Ethanol solvent was heated to around 50° C. and then polymers were dissolved therein by stirring with a mechanical stirrer to aid dispersion and dissolution of the polymers at a constant rpm. In particular, the polymer that is contained in a large amount and takes a long time to dissolve (for example, Glyceryl monooleate) was dissolved first and then other polymers were dissolved. Then, other ingredients and a medicinal ingredient were added thereto to make uniform solution or gel.

<Evaluation of Dissolution Rate and Remaining Amount>

1. Evaluation of Solubility in Hot and Humid Oral Condition without any Separate Physical Force In order to evaluate retention time in hot and humid oral condition, an artificial teeth made from a hydroxyapatite table (1 cm diameter) was fixed with silicone molding, and then 0.5 g of each of Examples 7 to 9 and Comparative Examples 8 to 12 was loaded thereon. Then, the time of complete dissolution when immersed in a thermohygrostat of 37° C. and 95% humidity was measured. A separate dissolution test was not carried out to Comparative Example 13 in the form of a patch.

2. Evaluation of Solubility in Artificial Saliva with Applied Physical Force Like Flowing Saliva An artificial teeth made from a hydroxyapatite table (1 cm diameter) was fixed with silicone molding, and then 1 g of each of Examples 7 to 9 and Comparative Examples 8 to 12 was loaded thereon. Then, in order to evaluate retention time by saliva, the time of complete dissolution when flowing the artificial saliva from top to bottom at a rate of 1 ml/min was measured.

3. Test Result

The results of evaluation of solubility in a hot and humid condition without a separate physical force and the results of evaluation of solubility in artificial saliva in which physical force like flowing saliva was applied were shown in the following Table 13.

TABLE 13

| Complete dissolution (disintegration) time | Exam. 7 | Exam. 8 | Exam. 9 | Comp. Exam. 8 | Comp. Exam. 9 | Comp. Exam. 10 | Comp. Exam. 11 | Comp. Exam. 12 |
|---|---|---|---|---|---|---|---|---|
| Left in condition of 37° C., 95% | >30 min | >30 min | >30 min | <6 min | <5 min | <5 min | 3 min | 2 min |
| Condition in which artificial saliva flows at a rate of 1 ml/min | >30 min | >30 min | >30 min | 15 min | 10 min | 15 min | 2 min | 1 min |

As can be seen from Table 13, it was confirmed that Example was not completely dissolved even after 30 min. However, it was confirmed from the results that Comparative Example was easily and completely dissolved.

<Panel Evaluation>

1. Survey for Clinical Sensitive Teeth or Gum Pain Relief
   1) Test subject and instructions: Examples 7 and 9 and Comparative Examples 8 and 10 to 12 were applied or attached to sensitive teeth or gum pain area for 10 min once a day and then removed.
   2) For each group, 15 volunteers who experienced sensitive teeth or gum pain were asked to use for 1 week and then survey was conducted according 5-point Likert scale.
   3) Scale Criteria
   5: Pain relief effect lasted for one month in all sensitive teeth or gum pain areas where the product was applied.
   4: Pain relief effect was definitely felt in all sensitive teeth or gum pain areas where the product was applied.
   3: Pain relief effect was definitely felt in at least one sensitive teeth or gum pain areas where the product was applied.
   2: Sensitive teeth against cold food was felt less sensitive, or gum pain was felt reduced, compared to before use.
   1: Sensitive teeth or gum pain relief effect was not felt.
2. Survey for Feeling of Whitening Effect to Human Subject
   1) Test subject and instructions: Example 8 and Comparative Examples 9 and 12 were attached to six teeth in the middle of the upper teeth for 30 min or longer once a day and then removed.
   2) For each group, 15 volunteers who felt the need for tooth whitening because they usually thinks that their teeth are yellow were asked to use for 1 week. Then, survey for feeling of whitening effect, compared to the unattached lower teeth, was conducted according 5-point Likert scale.
   3) Scale Criteria
   5: Compared to the unattached lower teeth, felt a definite whitening effect than before use within 5 days.
   4: Compared to the unattached lower teeth, felt that the teeth are definitely brighter than before use within 5 days.
   3: Compared to the unattached lower teeth, felt that the teeth are definitely brighter than before use after 1 week use.
   2: Compared to the unattached lower teeth, felt that the teeth are slightly brighter than before use.
   1: Felt no difference, compared to before use
3. Evaluation Result

TABLE 14

|  | Exam. 7 | Exam. 8 | Exam. 9 | Comp. Exam. 8 | Comp. Exam. 9 | Comp. Exam. 10 | Comp. Exam. 11 | Comp. Exam. 12 | Comp. Exam. 13 |
|---|---|---|---|---|---|---|---|---|---|
| Sensitive teeth improvement |  | 5 |  |  | 3 |  |  |  | 3 |
| Whitening effect | 4.5 |  |  | 3 |  |  |  | 2 |  |
| Gingivitis improvement |  |  | 4 |  |  | 2 | 2 |  |  |

As can be seen from Table 14, the preparations having composition of Examples of the present invention can have excellent efficacy by facilitating delivery of a medicinal ingredient and securing sufficient attachment time.

INDUSTRIAL APPLICABILITY

The present invention can be provided as an oral preparation which can be attached to teeth or tooth peripheries and the deliver a medicinal ingredient into the oral cavity. The preparation of the present invention is for attaching to teeth or tooth peripheries with excellent adhesive force.

The invention claimed is:

1. A preparation for attaching to teeth or tooth peripheries, wherein the preparation comprises polyvinyl alcohol, a salt, and an alginate compound, and optionally a synthetic silica,
   wherein the salt forms hydrogen bonds with —OH groups of the polyvinyl alcohol, and the preparation is in a slime hydrogel form before being attached to teeth or tooth peripheries, and
   wherein the alginate compound is contained in an amount of 0.1 wt % to 0.5 wt % based on a total weight of the preparation.

2. The preparation for attaching to teeth or tooth peripheries of claim 1, wherein the synthetic silica is at least one selected from silica powder, fumed silica, precipitated silica, colloidal silica, aerogel or silica sol.

3. The preparation for attaching to teeth or tooth peripheries of claim 1, wherein the alginate compound is calcium alginate, potassium alginate, sodium alginate, triethanolamine alginate or a mixture thereof.

4. The preparation for attaching to teeth or tooth peripheries of claim 1, wherein the salt forming hydrogen bonds with —OH groups of the polyvinyl alcohol is borate, phosphate or a mixture thereof.

5. The preparation for attaching to teeth or tooth peripheries of claim 1, which comprises a medicinal ingredient for intra-oral delivery, and the medicinal ingredient is sodium fluoride, stannous fluoride, indium fluoride, amine fluoride, sodium monofluorophosphate, tetrasodium pyrophosphate (TSPP), sodium acid pyrophosphate (SAPP), sodium tripolyphosphate (STP), sodium potassium pyrophosphate, tetrapotassium pyrophosphate, acidic sodium metaphosphate, acidic sodium polyphosphate, triclosan, chlorhexidine, alexidine, hexetidine, sanguinarine, benzalkonium chloride, salicylanilide, domiphen bromide, cetylpyridinium chloride (CPC), tetradecylpyridinium chloride (TPC), aspirin, ketorolac, flurbiprofen, piroxicam, meclofenamic acid, thiamine, riboflavin, nicotinic acid, pantothenic acid, pyridoxine, biotin, folic acid, vitamin B12, lipoic acid, ascorbic acid, vitamin A, vitamin D, vitamin E, vitamin K, titrated extract of *Zea Mays* L. unsaponifiable fraction, Magnoliae Cortex extract, Myrrha, Rhatany, Chamomile, policresulen, titrated extract of Centella Asiatica, nutmeg extract, dexpanthenol, β-sitosterol, acetyl salicylic acid, zinc chloride, potassium phosphate, potassium diphosphate, calcium chloride, oxalic acid, potassium oxalate, ferric oxalate or a mixture thereof.

6. The preparation for attaching to teeth or tooth peripheries of claim 1, wherein the synthetic silica is optionally comprised in an amount of 0.1 wt % to 10 wt % based on a total weight of the preparation.

7. The preparation for attaching to teeth or tooth peripheries of claim 1, wherein the synthetic silica is optionally comprised in an amount of 0.1 wt % to 2.4 wt % based on a total weight of the preparation.

\* \* \* \* \*